United States Patent [19]

Luther et al.

[11] Patent Number: 4,762,516
[45] Date of Patent: Aug. 9, 1988

[54] ASSEMBLY OF NEEDLE CATHETER PROTECTOR

[75] Inventors: Ronald B. Luther, Newport Beach; Pradip V. Choksi, Northridge, both of Calif.

[73] Assignee: Luther Medical Products, Inc., Santa Ana, Calif.

[21] Appl. No.: 22,132

[22] Filed: Mar. 5, 1987

[51] Int. Cl.⁴ .................................. A61M 5/00
[52] U.S. Cl. .................... 604/164; 604/168; 604/192; 604/198; 604/110
[58] Field of Search ............... 604/164–169, 604/158, 162, 263, 192, 198, 110

[56] References Cited

U.S. PATENT DOCUMENTS

| | | | |
|---|---|---|---|
| 3,463,152 | 8/1969 | Sorenson | 604/162 |
| 3,536,073 | 10/1970 | Farb | 604/162 |
| 4,160,450 | 7/1979 | Doherty | 604/162 |
| 4,500,312 | 2/1985 | McMarlane | 604/192 |
| 4,588,398 | 5/1986 | Daugherty et al. | 604/164 |
| 4,631,057 | 12/1986 | Mitchell | 604/198 |
| 4,676,783 | 6/1987 | Jagger et al. | 604/162 |
| 4,702,738 | 10/1987 | Spencer | 604/198 |

FOREIGN PATENT DOCUMENTS 0139872 8/1985 European Pat. Off. ............ 604/168

Primary Examiner—Dalton L. Truluck
Assistant Examiner—Denise Whelton
Attorney, Agent, or Firm—Stetina and Brunda

[57] ABSTRACT

An assembly of a needle and a device for protecting the needle tip is disclosed. The assembly comprises an elongate housing which mounts the needle. A needle guard is slidably mounted within the housing and is adapted to be moved forward along the needle. Following use, the needle and housing are retracted and the needle guard permanently locks with the housing while it occludes or covers the needle.

5 Claims, 3 Drawing Sheets

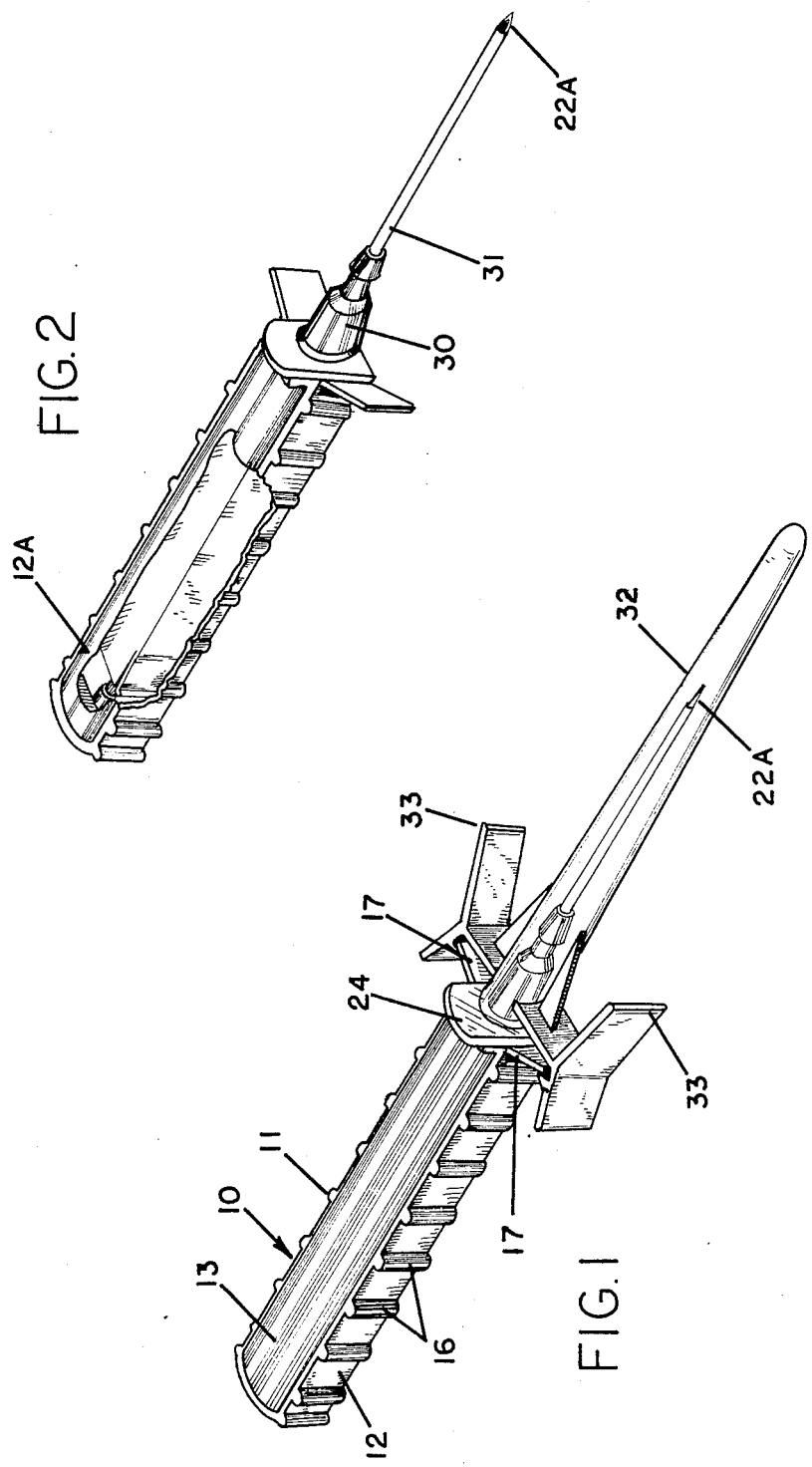

ASSEMBLY OF NEEDLE CATHETER PROTECTOR

BACKGROUND OF THE INVENTION

This invention relates to a new and improved assembly of a needle and a protective needle guard therefor.

Following use of a needle, they are usually broken and discarded to waste. However, there is always a small possibility that the discarded needle points may inadvertently stick or scratch medical health personnel. Also, it is desireable that persons who use or come in proximity to used needles will not have to contact them prior to, or subsequent to their use. This is becoming of increasing importance in reducing accidental infection from patients who have HTLV iii (AIDS) virus, hepatitis, and other infectious diseases.

There is presently on the market a device sold by ICU Medical which functions to almost completely enclose the needle subsequent to use. However, the device does not provide a housing or protective cover for the needle tip. This, of course, leaves open the possibility of a health care worker being accidentally stuck or scratched.

THE INVENTION

According to the invention, there is provided an assembly of a needle device and housing therefor, the housing providing an internally disposed needle guard which is adapted to slide forward outside the housing and completely enclose the needle following use. The needle guard is provided with flexible members which are adapted to permanently lock into the housing and ensure complete protection for the needle.

BRIEF DESCRIPTION OF THE DRAWINGS

FIG. 1 is an upper, external perspective view of the assembled device of this invention;

FIG. 2 is an upper, external perspective view, partly cut-away showing the slidable needle guard portion of the assembly;

DESCRIPTION OF THE PREFERRED EMBODIMENTS

Figure 3:
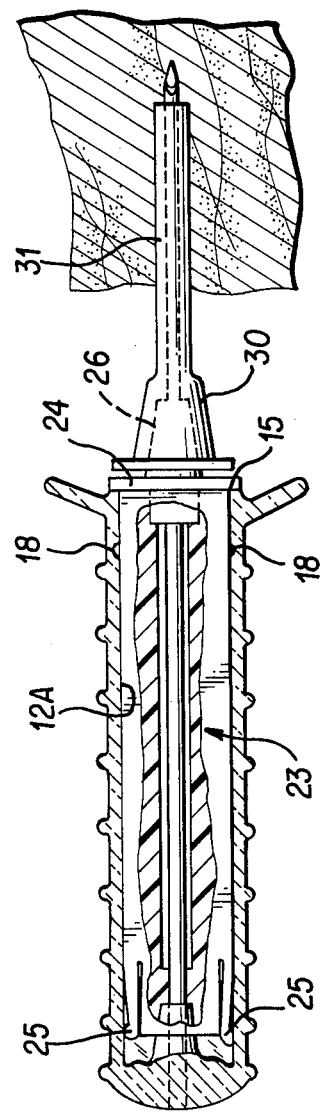
FIG. 3 is a cross sectional view in side elevation of the device, with the needle guard in the retracted position the needle and catheter being inserted into a patient.

The assembly 10 of this invention is shown in FIGS. 1 and 2 comprises a rectangular, elongate housing 11 of clear plastic such as injection molded polycarbonate or polystyrene. The clear plastic enables flashback to be readily observed. The housing provides enclosure walls 12 defining inside surfaces 12a, and a magnification portion 13 to better enable viewing blood flashback. At its closed end, a rear mount 14 in side the housing is adapted to mount and secure a needle. An open end 15 is defined by the housing through which the needle guard moves, and through which the needle projects. Fingergrip ridges 16 are provided on the exteriors of the walls, and these also serve to a certain extent to reinforce the housing structure. Stop wings 17 are provided at the open end 15 of the housing along with detent slots 18, the latter being designed to engage the needle guard.

A needle 22 having a bevelled tip 22a is secured within the housing 11 on the rear mount 14, the needle projecting through the open end 15 of the housing. A needle guard 23 is slidably mounted within the housing 11, and provides a forwardly located pull tab 24 and outwardly bent locking ears 25, 25. When the needle guard 23 is positioned in the housing 11, the locking ears 25, 25 are biased inwardly by contact with the inside surfaces 12a of the housing walls 12. The biasing is accomplished by using a plastic construction such as polystyrene, polycarbonate, etc., which have flexible properties in a thin wall form. A hub support 26 is provided by the needle guard through which the needle 22 projects. The combination of the fixed rear mount 14 and hub support 26 enables the needle to be maintained in alignment when it is thrust forward in use.

A luer-type locking hub 30 and attached catheter 31 are mounted on the hub support 26 and cover the needle, with only the needle tip 22a being exposed. A cover 32 having wings 33 is generally used to cover the luer-type-lock hub, catheter and needle to reduce loss of sterility and protect the user from the needle 22. The cover is secured to the device by a light interlock with the wings 17 of the housing 11.

Figure 3A:
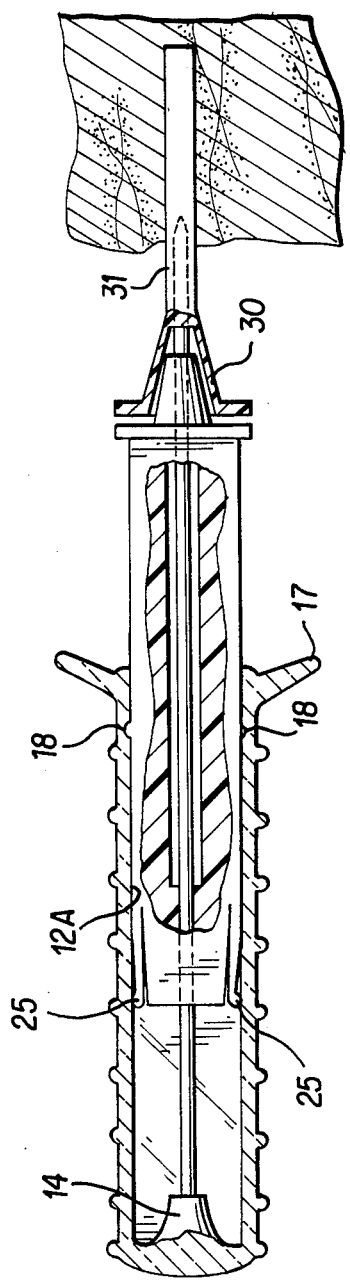
FIG. 3A is a cross sectional view in side elevation of the device, with the needle being partially retracted from the patient into the needle housing.

When the device is used, the cover 32 is removed, as shown in FIG. 2, and the needle 22 and catheter 31 are inserted into a patient as shown in FIG. 3. With the catheter remaining in the patient as shown in FIG. 3A, the needle can be withdrawn by pressing against the forward tab 24 while retracting the housing 11 to which the needle 22 is attached. Consequently, the needle guard 23 will slide forwardly until the locking ears 25 are clear of the inside surfaces 12a of the walls 22 of the housing. The locking ears will then revert to their normally outwardly extending configuration and lock into the detent slots 18 of the housing 11. This is shown in FIG. 4.

Figure 4:
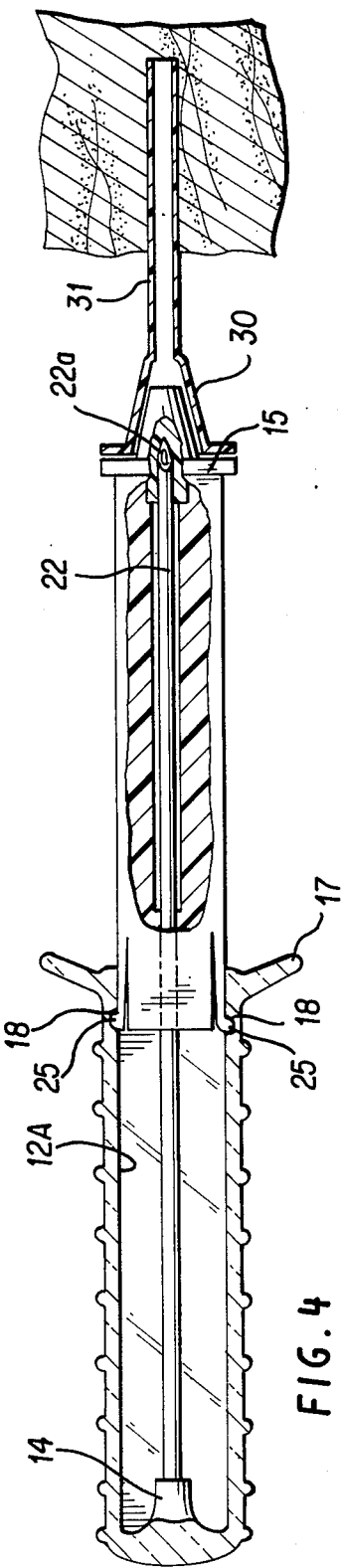
FIG. 4 is a cross sectional view in side elevation showing the needle guard in the extended position covering the needle, and being locked permanently into its associated housing.
Figure 5:
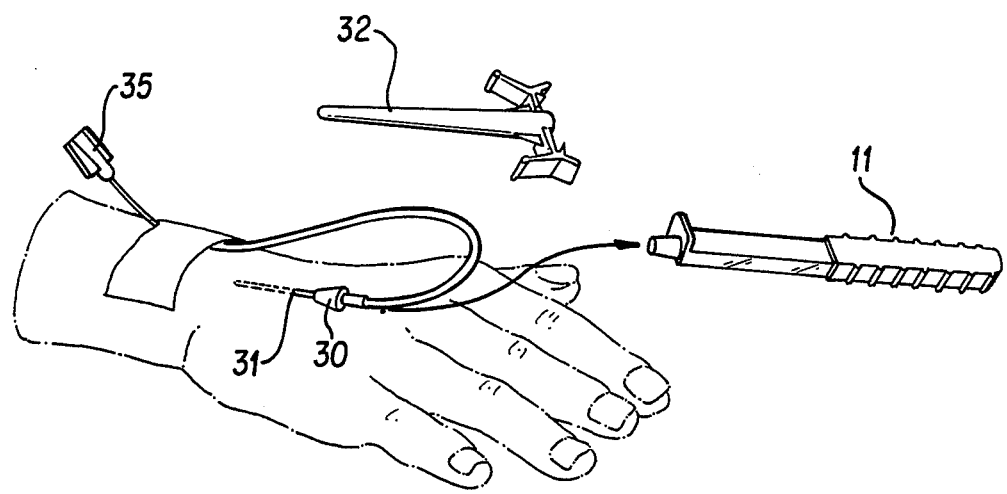
FIG. 5 is an external, perspective view of the device following separation of the hub and catheter from the housing and needle after the catheter has been inserted into a patient.

The needle guard is, or course, sized to accommodate the appropriate length of needle within the enclosure of the guard and within the forward bore element 26, as shown in FIG. 4, or within the enclosure of the guard. The hub 30 and attached catheter 31 are shown in FIG. 5 inserted into a patient and connected to an I.V. unit, while the needle 22 and housing 11 are shown following separation from the hub, catheter and patient. Since the needle guard and housing are now permanently engaged, the device can be disposed of without becoming a subsequent source of injury or infection to health care personnel.

It will also be appreciated that when the needle is retracted from the patient, it can be made to pass through the catheter and directly into the needle guard enclosure without any exposure to personnel, and this represents an additional safety feature.

It is apparent that many variations of this invention may be used while still remaining within the essential scope thereof. For example, there are many types of catheters which may be used insofar as materials are concerned. Thus, expandable, hydrophilic polymers, teflon, pvc, polyurethane, nylon, etc., all are available. Moreover, a wide range of needle sizes are usefully utilized in the assembly, and range from about 12-26 gauge.

We claim:

1. An assembly of a needle and protector therefor, comprising:
   a. an elongate housing providing sidewalls, and detent means defined thereon, the housing providing a rearwardly closed end and an open end;
   b. a needle mounted inside the housing and attached at one end to the closed end of the housing, and projecting through the open end of the housing;
   c. a needle guard slidably mounted within the housing, the needle guard having a pull tab at its forward end, and outwardly biased ears in contact with the sidewalls of the housing, the needle guard providing at its forward end a hub support defining a bore therein;
   d. a luer-type locking hub and catheter mounted on the hub support, the needle being aligned within the hub support, hub and catheter, and projecting through the catheter to expose a tip thereof;
   e. whereby, i. following insertion of the needle and catheter into a patient, the housing and attached needle are adapted to be retracted from the patient and the needle is adapted to be retracted into the needle guard thereby enabling the walls of the housing to slide relative the biased ears of the needle guard, the ears outwardly project into the detent means of the housing and permanently lock therewith, the needle guard being sized to completely enclose the needle upon locking with the housing;
   ii. the hub and catheter remain with the patient; and
   iii. the housing and enclosed needle are separated from the hub, catheter and patient.

2. The assembly of claim 1, in which housing and needle guard are constructed of polystyrene or polycarbonate resin.

3. The assembly of claim 1, in which the housing and needle guard are constructed of a clear plastic.

4. The assembly of claim 1, in which magnifying means are provided on the sidewall of the housing.

5. The assembly of claim 1, in which the catheter is constructed of a material selected from the class consisting of expandable polymers, teflon, polyurethane, pvc, and nylon.

* * * * *